United States Patent [19]

Kuwata et al.

[11] Patent Number: 4,987,169

[45] Date of Patent: Jan. 22, 1991

[54] METHOD OF PREPARING SILICON COMPOSITIONS

[75] Inventors: Satoshi Kuwata; Koji Sakuta; Shigeru Mori, all of Annaka, Japan

[73] Assignee: Shin-Etsu Chemical Co., Ltd., Tokyo, Japan

[21] Appl. No.: 341,744

[22] Filed: Apr. 21, 1989

[30] Foreign Application Priority Data

Apr. 22, 1988 [JP] Japan .................................. 63-101071
Mar. 9, 1989 [JP] Japan ..................................... 1-57378

[51] Int. Cl.$^5$ ................................................ C08K 5/54
[52] U.S. Cl. ...................................... 524/267; 524/731
[58] Field of Search .................................. 524/267, 731

[56] References Cited

U.S. PATENT DOCUMENTS 4,806,430 2/1989 Spielvogel et al. .................... 528/32

Primary Examiner—Melvyn I. Marquis
Attorney, Agent, or Firm—Oblon, Spivak, McClelland, Maier & Neustadt

[57] ABSTRACT

A method of preparing a uniform silicone composition, comprising treating under the application of a shearing force a polymeric product obtained by addition polymerization of (A) an organhydrogenpolysiloxane containing in its molecule from 1.5 to 5 silicon-bonded hydrogen atoms on average, said silicon-bonded hydrogen atoms being in an amount of from 1 to 20 mol %, based on the total of the silicon-bonded hydrogen atoms and silicon-bonded organic groups in the molecule; and (B) an organopolysiloxane containing in its molecule from 1.5 to 5 silicon-bonded aliphatic unsaturated groups on average; in the presence of from 10 to 1,000 parts by weight of low-viscosity silicone oil having a viscosity of not more than 100 cSt at 25° C. based on 100 parts by weight of the total amount of said (A) and (B).

16 Claims, 1 Drawing Sheet

METHOD OF PREPARING SILICON COMPOSITIONS

BACKGROUND OF THE INVENTION

1. Field of the Invention

This invention relates to a method of preparing a powdery, pasty or greasy silicone composition, and more particularly to a silicone composition useful as a thickening agent or the like.

2. Description of the Prior Art

Silicone oils, because of their safety and so forth, have been hitherto used as base oils for various compositions in a variety of fields including medical care and cosmetics. They, however, have been relatively highly viscous, usually having a viscosity of 100 cSt or more at 25° C.

In recent years, however, particularly in the fields of medical care and cosmetics, silicone oils with a low viscosity of 100 cSt or less have attracted notices because of their excellent spreadability, light feeling, high safety, etc., and comprehensive studies are made on their use. However, when, for example, a pasty or greasy silicone composition is prepared using the low-viscosity silicone oil as a base oil, a smooth and uniform composition can be obtained with difficulty because a thickening agent must be added in an increased amount, and there also has been involved the problem that the low-viscosity silicone oil is liable to be separated and discharged from the resulting composition. That is, the composition has low stability.

Accordingly, as thickening agents for the low-viscosity silicone oils, it has been hitherto proposed to use organic materials including fatty acid esters of dextrin (Japanese Unexamined Patent Publication (KOKAI) No. 121764/1987, No. 143971/1987, No. 143970/1987, and No. 159489/1988), fatty acid esters of sucrose (Japanese Unexamined Patent publication (KOKAI) No. 235366/1988), trimethylsilyl-substituted polyvinyl alcohols or trimethylsilyl-substituted polysaccharide (Japanese Unexamined Patent Publication (KOKAI) No. 240335/1987), and cellulose ethers containing a fatty acid ester group (Japanese Unexamined Patent Publication (KOKAI) No. 260956/1988).

It has been also proposed to use inorganic materials including organic material-modified clay minerals as the thickening agents (Japanese Unexamined Patent Publication (KOKAI) No. 45656/1987, No. 54759/1987 and No. 72779/1988).

However, use of the above organic materials as thickening agents brings about the problem that the properties such as light feeling and high spreadability may become inferior, which are inherent in the low-viscosity silicone oils. The above inorganic materials also have the disadvantage that they must be used in the presence of water and hence make poor the stability of the resulting composition.

SUMMARY OF THE INVENTION

Accordingly, an object of this invention is to provide a powdery, or pasty or greasy, silicone composition containing a low-viscosity silicone oil as a main component, having retained the features such as light feeling and spreadability, inherent in low-viscosity silicone oils, having a high stability, and useful as it is or as a compounding agent such as a thickening agent.

As disclosed herein, as a means for solving the problems involved in the prior art, this invention provides a method of preparing a silicone composition, comprising treating under application of shearing force a polymeric product obtained by addition polymerization of an organohydrogenpolysiloxane of (A) indicated below and an organopolysiloxane of (B) indicated below, in the presence of from 10 to 1,000 parts by weight of a low-viscosity silicone oil of (A) indicated below based on 100 parts by weight of the total amount of said (A) and (B). (A): An organohydrogenpolysiloxane containing in its molecule not less than 1.5 silicon-bonded hydrogen atoms in average.

(B) An organopolysiloxane containing in its molecule not less than 1.5 silicon-bonded aliphatic unsaturated groups in average.

(C) A low-viscosity silicone oil with a viscosity of not more than 100 cSt at 25° C.

The silicone composition obtained by the method of this invention is a powdery, or pasty or greasy, composition containing a low-viscosity silicone oil as a main component, and can be widely used as it is or as a compounding base agent or an additive. For example, because of its feeling, smoothness in appearance and good stability, and yet its superior safety and light feeling, the composition is useful for imparting light feeling to cream, caky molded products, etc. for cosmetics, quasi-drugs, etc. or improving spreadability.

In particular, when it is prepared in the form of paste or grease, it can be excellent in transparency, and a pigment as a material for cosmetics can be used without any limitation.

Also when prepared in the form of powder, it can be particularly easy to handle and have a very good lubricating property, so that, in addition to the cosmetics and quasidrugs, it is also useful for imparting lubricity, wear resistance, flexibility, impact resistance, etc. to rubbers, plastics and others by adding it to them.

The composition is still also useful as a thickening agent for not only the low-viscosity silicone oils but also low-viscosity hydrocarbon oils.

Also, no special preparation steps are required, and it has become possible to prepare highly transparent silicone paste or grease with ease. Moreover, a low-viscosity dimethyl silicone oil can be uniformly made greasy and it has become possible to maintain the high transparency in a wide wavelength region, so that the composition can be useful as an optical material.

The employment of a silicone oil with excellent low temperature properties as the silicone oil can give silicone grease that may get hard with difficulty even under conditions of low temperatures. Thus the composition in the form of the grease, having a stable consistency in a wide temperature range, can be used for low-temperature part sealing or lubrication in a variety of industrial equipments.

DETAILED DESCRIPTION OF THE INVENTION

Figure 1:
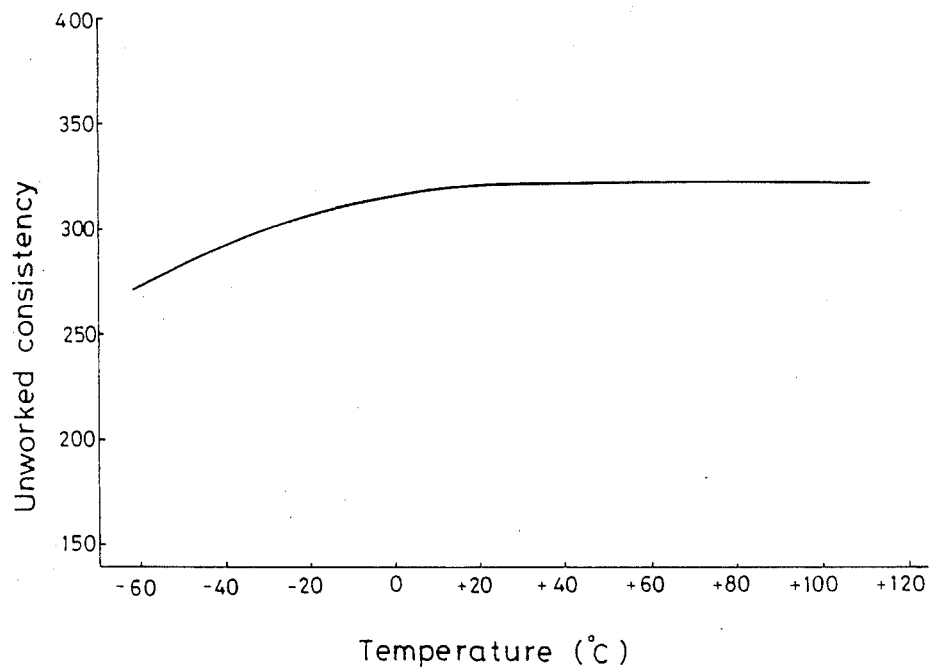
FIG. 1 is a view to show consistency-temperature changes of a greasy silicone composition obtained in Example 5.

In the method of this invention, the reactive organopolysiloxane of the components (A) and (B) are subjected to addition polymerization in the presence of the low-viscosity silicone oil of the component (C). so that the above polymerization product can be obtained in the state that the low-viscosity silicone oil has been incorporated into the three-dimensional crosslinked structure of the polymer formed.

The composition of this invention can be prepared in the form widely ranging from fine powder to paste, by adjusting the proportion of the starting materials to be used, and also by using together the same low-viscosity silicone oil as the above (C) when the above polymeric product is treated under application of shearing force.

This invention will now be described below in detail.

The (A) organohydrogenpolysiloxane used in this invention includes those comprising an $HSiO_{1.5}$ unit, an $RSiO_{1.5}$ unit, an RHSiO unit, an $R_2SiO$ unit, an $R_2HSiO_{0.5}$ unit or an $R_3SiO_{0.5}$ unit (wherein R is a substituted or unsubstituted monovalent hydrocarbon group except for an aliphatic unsaturated group, as exemplified by an alkyl group such as methyl, ethYl, propyl or butyl; an aryl group such as phenyl or tolyl; a monovalent hydrocarbon group including a cycloalkyl group such as cyclohexyl, and a substituted hydrocarbon group in which one or more hydrogen atoms possessed by &he monovalent hydrocarbon group have been substituted with a halogen atom such as chlorine, bromine or fluorine, a cyano group, e&c., as exemplified by a gamma-trifluoropropyl group and a chloromethyl group.) This component (A) organohydrogenpolysiloxane may be either straight-chain, branched, or cyclic, but may more preferably be linear or straight-chain to make the addition polymerization smoothly proceed.

This organohydrogenpolysiloxane contains in its molecule not less than 1.5, and preferably 2 to 5, silicon-bonded hydrogen atoms (Si—H bonds) in average.

The silicon-bonded hydrogen atoms in the molecule should preferably be in the proportion of usually from 0.5 to 50 mol %, and particularly from 1 to 20 mol %, based on the total of the silicon-bonded hydrogen atoms and organic groups.

The organic group (represented by R in the above) contained in the component (A) can include various groups, but may preferably be a methyl group, and it is particularly preferred that not less than 50 mol % of R's is comprised of methyl groups.

Typical examples of the above component (A) organohydrogenpolysiloxane include a compound represented by the formula:

$[(CH_3)_3SiO_{0.5}]_a[(CH_3)_2HSiO_{0.5}]_b[(CH_3)_2SiO]_c[CH_3HSiO]_d$, wherein a and b are each an integer of from 0 to 2, provided that a+b=2, c is an integer of from 0 to 500, and d is an integer Of from 0 to 50.

The component (A) may be in the form of a mixture of the compounds as described above, which can be preferably used.

The (B) organopolysiloxane containing an aliphatic unsaturated group contains in its molecule not less than 1.5, and preferably from 2 to 5; silicon-bonded aliphatic unsaturated groups in average. The aliphatic unsaturated group includes, for example. a vinyl group and an allyl group, but, in general, preferably a vinyl group. This organopolysiloxane includes, for example, those comprising an $(CH_2=CH)SiO_{1.5}$ unit, an $RSiO_{1.5}$ unit, an $R(CH_2=CH)SiO$ unit, an $R_2SiO$ unit, an $R_2(CH_2=CH)SiO_{0.5}$ unit or an $R_3SiO_{0.5}$ unit (wherein R is as defined above).

The molecular structure of this component (B) organopolysiloxane may be either straight-chain, branched, or cyclic, but may more preferably be straight-chain to make the addition polymerization smoothly proceed.

The aliphatic unsaturated groups, as exemplified by vinyl groups, should preferably be contained in an amount of from 0.5 to 50 mol %, and particularly from 1 to 20 mol %, of the silicon-bonded organic groups. The organic group other than the aliphatic unsaturated group may preferably include, for example, a methyl group, and, in particular, not less than 50 mol % of other organic groups should preferably be comprised of methyl groups.

Typical examples of the above component (B) organopolysiloxane include a methylvinylpolysiloxane represented by the formula:

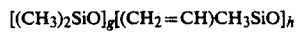

wherein e and f are each an integer of from 0 to 2, provided that e+f=2. g is an integer of from 0 to 500, and h is an integer of from 0 to 50, and the component (B) may be in the form of a mixture, which can be preferably used in this invention.

As described above, in either of the (A) organohydrogenpolysiloxane and the (B) organopolysiloxane, the number of the corresponding reactive groups, i.e., the silicon-bonded hydrogen atoms or aliphatic unsaturated groups, in the molecule is required to be not less than 1.5 in average. The number otherwise less than 1.5 for any one of them makes it difficult to form the three-dimensional structure in the polymer obtained by addition polymerization, resulting in a poorness in the intended thickening effect attributable to the low-viscosity silicone oil.

These reactive groups may preferably be contained in an amount of from 0.5 to 50 mol % in the respective polysiloxanes.

The content otherwise more than 50 mol % may result in an excessively high crosslink density in the three-dimensional structure formed by addition polymerization, making the (C) low-viscosity silicone oil be incorporated into the three-dimensional structure with difficulty, and the stability thereby became poor, e.g., the (C) low-viscosity silicone oil readily bleeding on its surface. On the other hand, the content otherwise less than 0.5 mol % also makes the (C) low-viscosity silicone oil be incorporated into the three-dimensional structure with difficulty because of the insufficient formation of the three-dimensional structure, or makes it impossible for a resulting silicone composition to be sufficiently thickened because the polymeric product becomes liable to be dissolved in the (C) low-viscosity silicone oil when the (C) low-viscosity silicone oil is used in a relatively large amount or when the (C) low-viscosity silicone oil is used as well in treating the resulting polymeric product under application of shearing force as described herein.

In a more preferred embodiment of this invention, at least one of the (A) organohydrogenpolysiloxane and the (B) organopolysiloxane containing the aliphatic unsaturated group contains the reactive groups in an amount smaller than 20 mol %. In this preferred embodiment, the degree of crosslinking of the polymer obtained by the addition polymerization is brought into a suitable state, and thus it is possible to obtain a composition that may cause the (C) low-viscosity silicone oil to be bleed out on the surface with difficulty. This is particularly advantageous when the composition is obtained in the form of powder. In the case when the composition is obtained in &he form of paste or grease, it is possible to obtain a composition that has been swelled in a good state with the (C) low-viscosity silicone oil treated together under application of shearing force, and yet may cause the low-viscositY silicone oil to be separated and discharged particularly with difficulty, thus having a very high stability.

Next, as the (C) low-viscosity silicone oil used in this invention, any silicone oil can be used without any particular limitation so long as it has a viscosity of not more than 100 cSt at 25° C., preferably not more than 50 cSt, and more preferably not more than 10 cSt. This viscosity otherwise more than 100 cSt may bring about a composition that may readily cause bleeding on the surface and has a low stability. It may also bring about sticky feeling, and thereby the light feeling is lowered.

Examples of the (C) low-viscosity silicone oil include siloxanes with a low degree of polymerization, including linear or branched ones such as methylpolysiloxane, methylphenylpolysiloxane, ethylpolysiloxane, ethylmethylpolysiloxane and ethylphenylpolysiloxane, and cyclic ones such as octamethylcyclotetrasiloxane and decamethylcyclopentasiloxane, one or more of which can be used under appropriate selection as occasion demands.

The composition of this invention is prepared by subjecting the (A) organohydrogenpolysiloxane and (B) organopolysiloxane to addition polymerization in the presence of the (C) low-viscosity silicone oil, where the (C) low-viscosity silicone oil is used in the proportion ranging from 10 to 1,000 parts by weight, and preferably ranging from 20 to 500 parts by weight, based on 100 parts by weight of the total amount of the (A) organohydrogenpolysiloxane and (B) organopolysiloxane. This is because the proportion of the low-viscosity silicone oil otherwise less than 10 parts by weight makes small the effect of using it together, so that the resulting composition may have a low viscosity. It also follows that the composition of this invention, which can be expected to give the effect of imparting flexibility and the effect of imparting lubricity when compounded into rubbers or plastics, may become short on these effects. It further follows that the resulting composition tends to lose its transparency when the polymeric product obtained is treated under application of shearing force together with the (C) low-viscosity silicone oil. On the other hand, the proportion of the (C) low-viscosity silicone oil otherwise more than 1000 parts by weight may result in a lowering of the reaction rate between the (A) organohydrogenpolysiloxane and (B) organopolysiloxane, making it impossible to obtain a polymeric product sufficiently thickened.

In particular, in the instance where the composition of this invention is obtained in the form of powder, the (C) low-viscosity silicone oil present when the addition-polymerization is carried out, may preferably be used in the proportion of from 10 to 200 parts by weight, particularly from 20 to 100 parts by weight, based on 100 parts by weight of the total weight of (A) and (B).

The (A) organohydrogenpolysiloxane and (B) organopolysiloxane may be used in the above addition polymerization preferably in the range of the proportion such that the molar ratio of the silicon-bonded hydrogen atoms possessed by (A) to the silicon-bonded aliphatic unsaturated groups possessed by (B) is from ½ to 3/1, and particularly preferably from ½ to 2/1. This ratio otherwise either excessively large or excessively small may impair the stability of the end composition because unreacted components (the silicon bonded hydrogen atoms or silicon-bonded aliphatic unsaturated groups) remain in the reaction product.

The above addition polymerization may be carried out in the presence of a platinum compound (as exemplified by chloroplatinate, alcohol-modified chloroplatinate; and a chloroplatinate-vinylsiloxane complex) or rhodium compound soluble to an organic solvent as exemplified by aliphatic alcohols such as methanol, ethanol, 2-propanol and butanol, aromatic hydrocarbons such as benzene, toluene and xylene, aliphatic or alicyclic hydrocarbons such as n-pentane, n-hexane and cyclohexane, and halogenated hYdrocarbons such as dichloromethane, chloroform, carbon tetrachloride, trichloroethane, trichloroethylene and hydrocarbon fluoride chloride, at room temperature or with heating (about 50° to 150° C.).

As catalysts, particularly preferred examples are chloroplatinate, the platinum compounds used in hydrosilylation reaction as described in U.S. Pat. Nos. 3,159,601, No. 159,662 and No. 3,775,452, etc., which preferably include, for example, a complex compound of vinylsiloxane with a platinum compound, and further the same having been modified with alcohol. Among these, particularly more preferred are the chloroplatinate described in U.S. Pat. No. 2,823,218. and a complex compound of vinylsiloxane with chloroplatinate.

The polymerization may be specifically operated by, for example, using a re action vessel such as a planetary mixer equipped with a suitable stirrer, mixing the respective (A), (B) and (C) organopolysiloxanes in given amounts, followed by further addition of a catalyst, and stirring the mixture at an appropriate temperature of from about 50° to about 150° C. Thus, the polymeric product can be readily obtained in the state that a polymer having the properties of being insoluble to the (C) low-viscosity silicone oil but sufficiently swelled by it has incorporated the (C) low-viscosity silicone oil coexisting in its inside. The above polymerization is carried out with stirring, using &he (C) low-viscosity silicone oil in the amount so adjusted that the polymeric product can be obtained in the form of powder, so that the reaction mixture is, as the polymerization reaction proceeds, gradually turned from a liquid into a soft mass and thereafter disintegrated until it is formed into powder.

Next, the polymeric product thus prepared is treated under application of shearing force.

In the instance where the composition of this invention is obtained in the form of powder, the polymeric product may be prepared in the form of powder as described above, and the resulting powder may be treated under application of shearing force as it is. Through this treatment the powdery polymeric product is further ground, and thus the composition of this invention can be obtained in the form of fine powder. This fine powder has uniform composition, and is generally a white powder, free from any bleeding seen on the surface, having smooth feeling, and endowed wi&h an appropriate degree of softness.

In the instance where the composition of this invention is prepared in the form of paste or grease, the mass-formed or powdery polymeric product obtained in the above may be treated under application of shearing force together with the (C) low-viscosity silicone oil in an amount of from 10 to 1,000 parts by weight, and preferably from 20 to 500 parts by weight, based on 100 parts by weight of said polymeric product. Through this treatment the product is kneaded, and thus the desired uniform composition can be obtained. Here, use of the (C) low-viscosity silicone oil in an amount less than 10 parts by weight based on 100 parts by weight of the polymeric product can not bring about any uniform pasty or greasy form, and also use thereof in an amount more than 1000 parts by weight can not give any resulting composition having been sufficiently thickened, similarly not bringing about any good pasty or greasy form. The treatment under application of shearing force is indispensable for obtaining a pasty or greasy composition which is relatively highly viscous, is uniform and has a smooth appearance, in spite of the use of the low-viscosity silicone oil. No or insufficient application of this shearing force may result in insufficient swelling of the polymeric product with the low-viscosity silicone oil, with the result that the both components remain unintimately mixed, so that the resulting composition becomes non-uniform, has a low viscosity in itself, and have insufficient ability of thickening. Since an insufficiently swelled polymeric product remains in the composition, the composition has rough feeling and is not smooth in appearance.

The treatment carried out under application of shearing force can be carried out using, for example, a three-roll mill, a two-roll mill, a sand grinder, a colloid mill, and a Gaulin homogenizer, which may be selected depending on the properties or the like of the product to be treated. In particular, preferred is to carry out the treatment by use of a three-roll mill.

EXAMPLES

This invention will be further described by giving Examples. These, however, by no means limit this invention. Viscosity set out in Examples refers to the viscosity at 25° C., and consistency was measured according to JIS K2220.

EXAMPLE 1

In a planetary mixer with an internal volume of about 5 liter, 600 g of trimethylsilyl-terminated dimethylmethylhydrogenpolysiloxane (average molecular weight: 2,280; Si—H: 3.1 mol %), 267 g of dimethylvinylsilyl-terminated dimethylpolysiloxane (average molecular weight: 930; vinyl group: 7.7 mol %) and 1,300 g of dimethylpolysiloxane (viscosity: 6 cSt) were mixed with stirring. In the resulting mixed solution, 0.5 g of a 2% chloroplatinate solution in 2-propanol was added, and stirring was continued at 70 to 80° C. for 2 hours. Polymeric product I, obtained as a result, was a powdery product endowed with softness.

After 100 parts by weight of this polymeric product I and 150 parts by weight of dimethylpolysiloxane (viscosity: 6 cSt) were mixed by dispersion, the mixture was thoroughly kneaded under application of shearing force using a three-roll mill to effect swelling. Thus preparing a silicone composition. This silicone composition was colorless and transparent in appearance and had a viscosity of 40,000 cp.

For comparison, a mixture comprising 100 parts by weight of the polymeric product I mixed in the same way as the above and 150 parts by weight of dimethylpolysiloxane (viscosity: 6 cSt) was stirred at room temperature for 2 hours by using a planetary mixer in place of the three-roll mill. However, the resulting silicone composition had only a viscosity of 6,000 cP, a rough feeling remained, and no pasty composition with a smooth feeling was obtainable.

Thus, the application of sufficient shearing force with use of the three-roll mill made it possible to achieve uniform swelling of the polymeric product powder with the silicone oil to obtain a pasty composition having been highly thickened and having a smooth feeling, but such a pasty composition was not obtainable under conditions in which no shearing force was applied.

COMPARATIVE EXAMPLE 1

Example 1 was repeated to obtain polymeric product II as a powder, except that the materials charged in the planetary mixer were comprised of 1600 g of trimethylsilyl-terminated dimethylmethylhydrogenpolysiloxane (average molecular weight: 2,280; Si—H: 3.1 mol %), 712 g of dimethylvinylsilyl-terminated dimethylpolysiloxane (average molecular weight: 930; vinyl group: 7.7 mol %) and 1.2 g of a 2% chloroplatinate solution in 2-propanol.

Example 1 was further repeated to obtain a silicone composition, except that 100 parts by weight of this polymeric product II and 525 parts by weight of dimethylpolysiloxane (viscosity: 6 cSt) were mixed, in other words, they were so mixed that the amount of the crosslinked silicone polymer contained in the end composition may be the same as that of Example 1. This silicone composition was cloudy in appearance and had a viscosity of 1,100 cp Thus, in the instance where the low-viscosity silicone oil (viscosity: 6 cSt) is not present together when the polymerization is carried out, it is clear that the final composition is cloudy in appearance and is poorly thickened.

EXAMPLE 2

Example 1 was repeated to obtain polymeric product III as a powder, except that, as the charge materials. 320 g of trimethylsilyl-terminated dimethylmethylhydrogenpolysiloxane (average molecular weight: 2,870; Si—H: 2.5 mol %). 616 g of dimethylvinylsilyl-terminated dimethylpolysiloxane (average molecular weight: 5,000; vinyl group: 1.5 mol %) and 1,405 g of dimethylpolysiloxane (viscosity: 50 cSt) were mixed, and 0.5 g of a 2 % chloroplatinate solution in 2-propanol was added.

Example 1 was further repeated to obtain a silicone composition, except that 100 parts by weight of this polymeric product III and 60 parts by weight of dimethylpolysiloxane (viscosity: 50 cSt) were mixed.

This silicone composition was colorless and transparent in appearance, and greasy, with an unworked consistency of 370 and a worked consistency of 370.

COMPARATIVE EXAMPLE 2

Example 2 was repeated to obtain polymeric product IV as a powder, except that, as the charge materials, 840 g of trimethylsilyl-terminated dimethylmethylhydrogenpolysiloxane (average molecular weight: 2,870; Si—H: 2.5 mol %) and 1,617 g of dimethylvinylsilyl-terminated dimethylpolysiloxane (average molecular weight: 5,000: vinyl group: 1.5 mol %) were mixed, and 1.2 g of a 2% chloroplatinate solution in 2-propanol was added.

Example 1 was further repeated to thoroughly carry out the kneading, except that 100 parts by weight of this polymeric product IV and 300 parts by weight of dimethylpolysiloxane (viscosity: 50 cSt) were mixed, in other words, they were so mixed that the amount of the crosslinked silicone polymer contained in the end composition may be the same as that of Example 2. However, no uniform silicone composition could be obtained.

Thus, in the instance where the low-viscosity silicone oil (viscosity: 50 cSt) is not present together when the polymerization is carried out, it is seen that no uniform silicone composition is obtainable.

EXAMPLE 3

Example 1 was repeated to obtain polymeric product V as a powder, except that, as the charge materials, 250 g of dimethylhydrogensilyl-terminated dimethylpolysiloxane (average molecular weight: 2,280; Si—H: 3.mol %), 613 g of trimethylsilyl-terminated dimethylmethylvinylpolysiloxane (average moledular weight: 5,000; vinyl group: 1.5 mol %) and 1,294 g of dimethylpolysiloxane (viscosity: 6 cSt) were mixed, and 0.5 g of a 2% chloroplatinate solution in 2-propanol was added.

Example 1 was further repeated to obtain a silicone composition, except that 100 parts by weight of this polymeric product V and 150 parts by weight of dimethylpolysiloxane (viscosity: 6 cSt) were mixed.

This silicone composition was colorless and transparent in appearance, and greasy, with an unworked consistency of 360 and a worked consistency of 365. Transmittance of visible light was also measured to find that the composition showed a transmittance of 90% or more over a wavelength region of from 340 to 700 nm.

EXAMPLE 4

Example 1 was repeated to obtain polymeric product VI as translucent, soft and small masses, except that, as the charge materials, 146 g of trimethylsilyl-terminated dimethylmethylhydrogenpolysiloxane (average molecular weight: 2,280; Si—H: 3.1 mol %), 3.55 g of dimethylvinylsilyl-terminated dimethylpolysiloxane (average molecular weight: 5,000; vinyl group: 1.5 mol %) and 2,000 g of octamethylcyclotetrasiloxane (viscosity: 2.3 cSt) were mixed, and 0.3 g of a 2% chloroplatinate solution in 2-propanol was added.

Example 1 was further repeated to obtain a silicone composition, except that 100 parts by weight of this polymeric product VI and 100 parts by weight of octamethylcyclotetrasiloxane were mixed.

This silicone composition was colorless and transparent in appearance, and greasy. Further, 100 parts by weight of this silicone composition and 100 parts by weight of octamethylcyclotetrasiloxane were mixed, and the mixture was dissolved with stirring at room temperature for 1 hour to obtain a colorless and transparent, and viscous silicone composition (viscosity: 9,000). This showed a heat loss of 95% at 150° C. after 30 minutes, and thus a stable silicone composition was seen to have obtained from a very small amount of a crosslinked silicone polymer.

EXAMPLE 5

Example 1 was repeated to obtain polymeric product VII as a powder, except that, as the charge materials, 250 g of dimethylhydrogensilyl-terminated dimethylpoly-siloxane (average molecular weight: 2,280; Si—H: 3.1 mol %), 613 g of trimethylsilyl-terminated dimethylmethylvinylpolysiloxane (average molecular weight: 5,000; vinyl group: 1.5 mol %) and 1,294 g of methylpolysiloxane (viscosity: 19 cSt) comprising (CH$_3$)$_3$SiO$_{0.5}$ units, (CH$_3$)$_2$SiO units and CH$_3$SiO$_{1.5}$ units in the proportion of 1:1:1 were mixed, and 0.5 g of a 2% chloroplatinate solution in 2-propanol was added.

Example 1 was further repeated to give a silicone composition, except that 100 parts by weight of this polymeric product VII and 150 parts by weight of methylpolysiloxane (viscosity: 19 cSt) were mixed.

This silicone composition was colorless and transparent in appearance, and greasy, with an unworked consistency of 324 and a worked consistency of 324. Consistency-temperature changes were measured to obtain the results as shown in FIG. 1. An abrupt lowering of consistency, i.e., hardening, was little observed even at −60° C., showing a very good low-temperature property.

EXAMPLE 6

Example 1 was repeated to obtain polymeric product& VIII as a powder, except that, as the charge materials, 250 g of trimethylsilyl-terminated dimethylmethylhydrogenpolysiloxane (average molecular weight: 2,280; Si—H: 3.1 mol %), 613 g of dimethylvinylsilyl-terminated dimethylpolysiloxane (ave rage molecular weight: 5,000; vinyl group: 1.5 mol %) and 1,294 g of phenyltris(trimethylsiloxy)silane (viscosity: 3.8cSt) were mixed, and 0.5 g of a 2% chloroplatinate solution in 2-propanol was added.

Example 1 was further repeated to obtain a silicone composition, except that 100 par&s by weight of this polymeric product VIII and 270 parts by weight of phenyltris(trimethylsiloxy)silane were mixed.

This silicone composition was smooth in appearance, and had excellent spreadability, with a viscosity of 66,000 cP.

EXAMPLE 7

Example 1 was repeated to obtain polymeric product IX as a powder, except that, as the charge materials, 320 g of dimethylhydrogensilyl-terminated dimethylpolysiloxane (average molecular weight: 2,870; Si—H: 2.5 mol %), 616 g of trimethylsilyl-terminated dimethylmethylvinylpolysiloxane (average molecular weight: 5,000; vinyl group: 1.5 mol %) and 1,405 g of octamethylcyclotetrasiloxane were mixed, and 0.5 g of a 2% chloroplatinate solution in 2-propanol was added.

Example 1 was further repeated to obtain a silicone composition, except that 100 parts by weight of this polymeric product IX and 300 parts by weight of methyltristrimethylsiloxane were mixed.

This silicone composition was colorless and transparent in appearance, and greasy, with a viscosity of 100,000 cP.

EXAMPLE 8

Example 1 was repeated to obtain polymeric product X as a powder, except that, as the charge materials, 30 g of trimethylsilyl-terminated dimethylmethylhydrogenpolysiloxane (average molecular weight: 11,200; Si—H: 18.4 mol %), 1,140 g of dimethylvinylsilyl-terminated dimethylpolysiloxane (average molecular weight: 14,200: vinyl group: 0.52 mol %) and 1,170 g of octamethyltrisiloxane (viscosity: 1.0 cSt) were mixed, and 0.5 g of a 2% chloroplatinate solution in 2-propanol was added.

Example 1 was further repeated to obtain a silicone composition, except that 100 parts by weight of this polymeric product X and 200 parts by weight of octamethyltrisiloxane were mixed.

This silicone composition was colorless and transparent in appearance, with a viscosity of 12,000 cP.

EXAMPLE 9

In a planetary mixer with an internal volume of about 5 liter, 650 g of trimethylsilyl-terminated dimethylmethylhydrogenpolysiloxane (average molecular weight: 2,180; Si—H content: 6.5 mol %); 549 g of dimethylvinylsilyl-terminated dimethylpolysiloxane (average molecular weight: 930; vinyl group content: 7.7 mol %) and 800 g of octamethylcyclotetrasiloxane (viscosity: 2.3 cSt) were mixed with stirring. In the resulting mixed solution, 0.5 g of a 2-propanol 2% chloroplatinate solution was added, and stirring was continued at 70° to 80° C. for 2 hours. As a result, there was obtained a white powder endowed with softness. This powder was further ground using a three-roll mixer to obtain a uniform, white powder composition as polymeric product XI.

The powder obtained was an agglomerated powder with an irregular shape, a moisture-free and dried surface and a particle diameter of about 100 to 500 micrometers, having a soft feeling. This was very good to feel, and readily disintegrated into fine particles of about 10 to 20 micrometers when slightly rubbed with fingers, to show excellent lubricity.

EXAMPLE 10

The polymeric product XI obtained in Example 9 and octamethylcyclotetrasiloxane were mixed in the mixing make-up as shown in Table 1, in a planetary mixer with an internal volume of about 5 liter, and the mixtures were each stirred at room temperature for 2 hours to readily obtain slightly white, pasty compositions.

The resulting compositions were all smooth, and were very softly spreadable when spread on the skin.

TABLE 1

| No. | Mixing make-up (g) | | Viscosity (cP) |
| --- | --- | --- | --- |
| | Polymeric product XI | Octamethylcyclo-tetrasiloxane | |
| 1 | 300 | 700 | 43,000 |
| 2 | 270 | 730 | 9,800 |
| 3 | 230 | 770 | 210 |

COMPARATIVE EXAMPLE 3

Example 9 was entirely repeated to obtain a polymeric product XII as a powder, except that the octamethylcyclotetrasiloxane was omitted.

The resulting powder was somewhat fairly hard and was bad to feel. In the same manner as Example 10, 300 g of the polymeric product XII and 700 g of octamethylcyclotetrasiloxane were also mixed in a planetary mixer having an internal volume of about 5 liter, and the mixture was stirred at room temperature for 2 hours. However, there was only obtained an unsmoothed, non-uniform composition, also with a viscosity of 150 cP. showing a poor thickening effect.

EXAMPLE 11

In a planetary mixer with an internal volume of about 5 liter, 880 g of trimethylsilyl-terminated dimethylmethylhydrogenpolysiloxane (average molecular weight: 2,340; Si—H content: 4.5 mol %), 512 g of dimethylvinylsilyl-terminated dimethylpolysiloxane (average molecular weight: 930; vinyl group content: 7.7 mol %) and 597 g of phenyltris(trimethylsiloxy)silane (viscosity: 3.8 cSt) were mixed with stirring, in the same manner as Example 9. In &he resulting mixed solution, 0.5 g of a 2% chloroplatinate solution in 2-propanol was added, followed by entirely the same procedures as Example 9 to obtain a white powder composition. The powder obtained had a moisture-free, dried surface, was good to feel, and showed excellent lubricity.

EXAMPLE 12

In a planetary mixer with an internal volume of about 5 liter, 660 g of dimethylhydrogensilyl-terminated dimethylpolysiloxane (average molecular weight: 1.020; Si—H content; 6.7 mol %), 1,135 g of trimethylsilylterminated dimethylmethylvinylpolysiloxane (average molecular weight: 2,640; vinyl group content: 4.2 mol %) and 199 g of trimethylsilyl-terminated dimethylpolysiloxane (viscosity: 6 cSt) were mixed with stirring, in the same manner as Example 9. In the resulting mixed solution, 0.5 g of a 2-propanol 2% chloroplatinate solution was added, followed by entirely the same procedures as Example 9 to obtain a white powder composition. The powder obtained had a moisture free, dried surface, was good to feel, and showed excellent lubricity.

COMPARATIVE 4

In Example 9, the thickening effect was confirmed using the powder composition not having been ground by the three-roll mill. Namely, 300 g of the above powder composition and 700 g of octamethylcyclotetrasiloxane were mixed in a planetary mixer having an internal volume of about 5 liter, and the stirring was carried out at room temperature for 2 hours in the same manner as Example 10. However, there was only obtained an unsmoothed, non-uniform composition, also with a viscosity of 520 cP, showing a poor thickening effect.

we claim:

1. A method of preparing a uniform silicone composition, comprising treating under the application of a shearing force a polymeric product obtained by addition polymerization of (A) on organohydrogenpolysiloxane containing in its molecule from 1.5 to 5 silicon-bonded hydrogen atoms on average, said silicon-bonded hydrogen atoms being in an amount of from 1 to 20 mol %, based on the total of the silicon-bonded hydrogen atoms and silicon-bonded organic groups in the molecule; and (B) an organopolysiloxane containing in its molecule from 1.5 to 5 silicon-bonded aliphatic unsaturated groups on average; in the presence of from 10 to 1,000 parts by weight of low-viscosity silicone oil having a viscosity of not more than 100 cSt at 25° C. based on 100 parts by weight of the total amount of said (A) and (B).

2. The method according to claim 1, wherein said polymeric product is treated under said application of shearing force, together with from 10 to 1,000 parts by weight of the same low-viscosity silicone oil as the above (C), and said silicone composition is obtained in the form of paste.

3. The method according to claim 1, wherein said addition polymerization is carried out with stirring, in the presence of from 10 to 200 parts by weight of said component (C) low-viscosity silicone oil, and said silicone composition is obtained in the form of powder.

4. The method according to claim 1, wherein said organohydrogenpolysiloxane (A) has the formula.

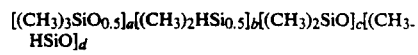

wherein a and b are each an integer of from 0 to 2, provided that a+b=2, small c is an integer of from 0 to 500 and d is an integer of from 0 to 50.

5. The method according to claim 1, wherein said organopolysiloxane (B) has the formula:

$$[(CH_2=CH)(CH_3)_2SiO_{0.5}]_e[(CH_3)_3SiO_{0.5}]_f$$

$$[(CH_3)_2SiO]_g[(CH_2=CH)CH_3SiO]_h$$

wherein, e and f are each an integer of from 0 to 2, provided that e+f=2, g is an integer from 0 to 500 and h is an integer of from 0 to 50.

6. The method according to claim 1, wherein said low-viscosity silicone oil has a viscosity of not more than 50 cSt at 25° C.

7. The method according to claim 1, wherein said low-viscosity silicone oil has a viscosity of not more than 10 cSt at 25° C.

8. The method according to claim 1, wherein said organohydrogenpolysiloxane (A) is in the form of a mixture of compounds.

9. The method according to claim 1, wherein said organopolysiloxane (B) is in the form of a mixture of compounds.

10. The method according to claim 1, wherein a molar ratio of silicon-bonded hydrogen atoms of (A) to the silicon-bonded aliphatic unsaturated groups of (B) is from ⅓ to 3/1.

11. The method according to claim 1, wherein said low-viscosity silicone oil is a siloxane having a low degree of polymerization selected from the group of methylpolysiloxane, dimethylpolysiloxane, methylphenylpolysiloxane, ethylpolysiloxane, ethylmethylpolysiloxane, ethylphenylpolysiloxane, octamethylcyclotetrasiloxane and decamethylcyclopentasiloxane and mixtures thereof.

12. The method according to claim 1, which further comprises effecting said reaction in the presence of a platinum compound or a rhodium compound, as a catalyst, in a solvent.

13. The method according to claim 1, wherein said compound (A) is selected from the group consisting of trimethylsilyl-terminated dimethylmethylhydrogenpolysiloxane, dimethylhydrogensilyl-terminated dimethylpolysiloxane and trimethylsilyl-terminated dimethylmethylhydrogenpolysiloxane.

14. The method according to claim 1, wherein said compound (B) is selected from the group consisting of dimethylvinylsilyl-terminated dimethylpolysiloxane and trimethylsilyl-terminated dimethylmethylvinylpolysiloxane.

15. The method according to claim 1, wherein said low-viscosity silicone oil is selected from the group consisting of phenyltris(trimethylsiloxy) silane and octamethyltrisiloxane.

16. The method according to claim 1, wherein said catalyst is chloroplatinate.

* * * * *